United States Patent [19]

Berninger et al.

[11] 4,196,352

[45] Apr. 1, 1980

[54] MULTIPLE PURPOSE HIGH SPEED TOMOGRAPHIC X-RAY SCANNER

[75] Inventors: Walter H. Berninger; Rowland W. Redington, both of Schenectady, N.Y.

[73] Assignee: General Electric Company, Schenectady, N.Y.

[21] Appl. No.: 900,781

[22] Filed: Apr. 28, 1978

[51] Int. Cl.² ............................................. G03B 41/16
[52] U.S. Cl. .................................. 250/445 T; 250/360
[58] Field of Search ............................ 250/445 T, 360

[56] References Cited

U.S. PATENT DOCUMENTS

| 4,031,395 | 6/1977 | Le May | 250/445 T |
| 4,057,725 | 11/1977 | Wagner | 250/445 T |
| 4,135,095 | 1/1979 | Watanabe | 250/445 T |

Primary Examiner—Craig E. Church
Attorney, Agent, or Firm—Lawrence D. Cutter; James C. Davis; Marvin Snyder

[57] ABSTRACT

A multiple source, rotating, tomographic x-ray scanner includes x-ray sources adaptably configurable to operate in two modes. The first mode of operation, in which the sources are planarly configured, permits high speed, single slice scans to be made. The second mode of operation in which the x-ray sources are configured so as to scan distinct, but contiguous planes, permits multiple slices to be made in a single scan.

5 Claims, 6 Drawing Figures

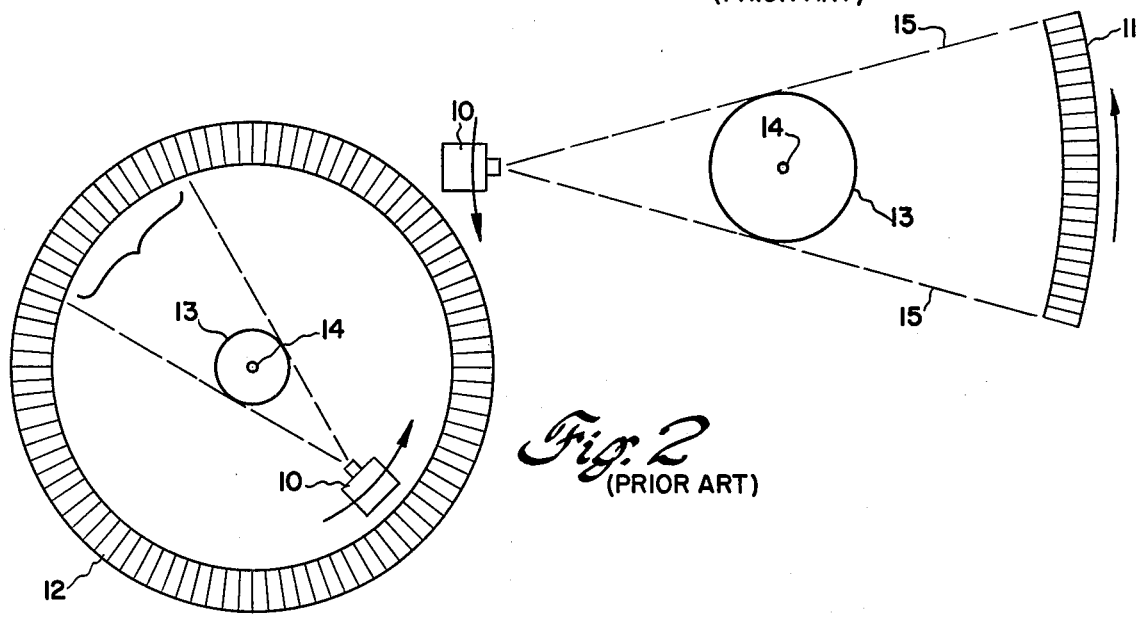
*Fig. 1* (PRIOR ART)
*Fig. 2* (PRIOR ART)
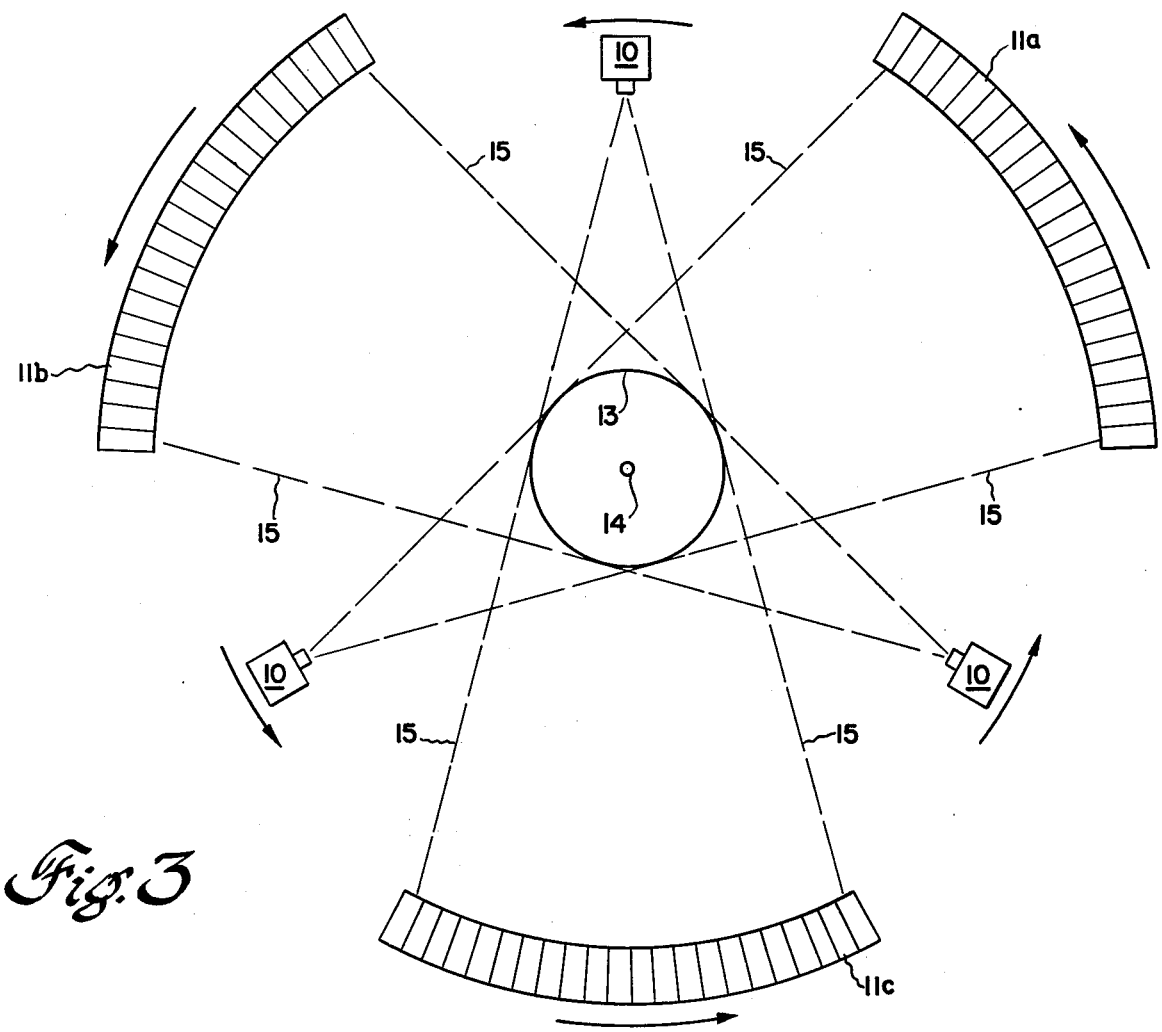
*Fig. 3*

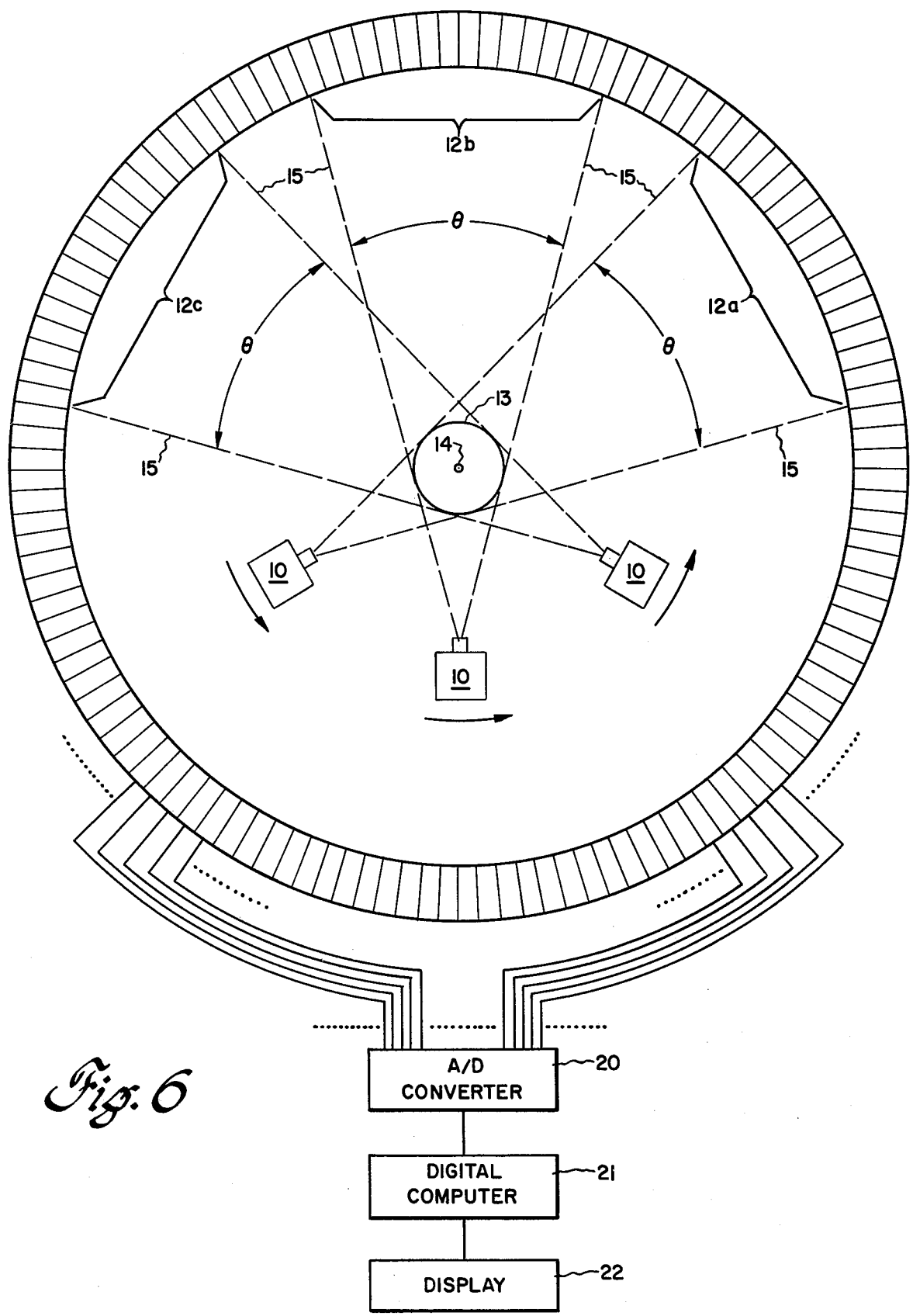

MULTIPLE PURPOSE HIGH SPEED TOMOGRAPHIC X-RAY SCANNER

BACKGROUND OF THE INVENTION

This invention relates to computerized tomographic x-ray scanners. More particularly, this invention relates to multiple purpose scanning systems capable of performing high-speed, single slice imaging, or slower multiple slice imaging.

In computerized tomographic applications, the body to be studied is disposed between an x-ray source and a plurality of x-ray detectors. The x-ray source typically produces a relatively flat, fan-shaped beam of x-rays, or other penetrating radiation, which ultimately impinges upon the detectors after having been modulated by the body under study. During irradiation, data representing relative intensities of radiation impinging upon the detectors are collected and stored. Typically, the x-ray source is caused to irradiate the body from a plurality of directions, each direction defining a particular view. Most often, the irradiation directions are distributed uniformly about a circumference surrounding the body under study. After each irradiation, the data representing the relative x-ray intensities are collected and stored, usually in a digital computer system, following analog-to-digital conversion of the electrical signals generated by the detectors in response to the x-ray irradiation.

The data collected are then analyzed by the digital computer system which generates an array of numbers representing the relative x-ray absorption at a corresponding array of points in a plane of the body through which the x-ray fan beam passes. The array of numbers corresponds to grey scale levels represented in the resultant x-ray image. In this way, an x-ray picture representing a slice through the body under study is generated. In contrast to conventional x-ray systems, tomographic x-ray systems produce shadow-free images. This shadow-free characteristic stems directly from the fact that a plurality of scans are made from differing directions and from the fact that a digital computer is utilized to independently determine the coefficient of absorption of a rectangular array of points (picture elements or pixels) located within a plane of the body under study. Typical tomographic image resolutions approach a million pixels arranged in a 1,000 by 1,000 array with each picture element capable of representing approximately one thousand different signal levels (grey scale values).

These tomographic imaging systems are most widely used for medical diagnostic purposes and in particular for the detection of human tumors. However, these imaging systems are also used in other industrial applications and at relatively high levels of x-ray intensity when biological forms are not subjected to the x-ray beams.

Because of the relatively slow scan speed, the medical uses for tomographic imaging systems were originally limited to images such as brain scans, where it is possible to secure the patient's head in an immobile position for a time sufficient to complete the scan of a single slice. More recent tomographic imaging systems are able to work at an increased scanning rate, thereby permitting tomographic imaging of such internal human organs as the lungs, liver, kidneys and pancreas. However, in some such systems, the patient is required to hold his breath for periods of twenty or more seconds. For a critically ill patient, or for patients with certain diseases, this breath holding can be difficult, strenuous, or impossible.

Moreover, for studies of cardiac functions in which there is no patient control over cardiac motion, or cardiac rates, the typical tomographic imaging system fails to provide sufficiently rapid scans. The cardiac rate is simply too fast for most scanning processes which generate and accumulate data in serial rather than parallel fashion. Thus, certain dynamic blood flow studies, important in a variety of kidney and cardiovascular dysfunctions, cannot be analyzed by current tomographic imaging systems because the scan time is too long to resolve the flow of blood through the volume of interest. Even in non-dynamic studies of the heart, image quality and the ability to detect small differences in absorption coefficient is degraded, due to excessive presence of motion, thereby blurring the image.

While scan speed is important in the above-described situations, it also is desirable to have a system capable of generating multiple, contiguous slices so that an adequate cross-sectional representation of the organ, or organs, under study may be produced.

SUMMARY OF THE INVENTION

In accordance with a preferred embodiment of the invention, a plurality of rotatable x-ray sources is provided. These x-ray sources are disposed about a circumference surrounding the body under study and are adaptable to be moved in a direction perpendicular to the plane containing the circumference. In this way, the sources are reconfigurable so that a plurality of contiguous slices may be scanned simultaneously, the number of slices being equal to the number of sources. There must, of course, be an integer number of x-ray sources and typically the number chosen is either 3, 5, or 7.

When the x-ray sources are configured in a planar geometry, they are arranged with respect to the detectors in a nonoverlapping fashion so that the x-ray sources may be fired simultaneously, thereby generating data in a parallel fashion. In this way, simultaneous viewings may be had from a plurality of directions. Thus, if a single source, prior art form of tomographic imaging system requires a time $T_O$ for a complete 360° scan, then the imaging system of the present invention, with the n sources configured in the same plane, requires a total scan time of only $T_O/n$.

The x-ray sources of the present invention, however, are movable in a direction parallel to the axis of rotation so as to be reconfigurable, in that the x-ray sources can be made to rotate in distinct contiguous planes. This permits the generation of n tomographic image slices in the same time as previously required for a single slice. While this does not have as significant an impact on scan time, it does greatly increase patient throughput, especially in those cases requiring multiple contiguous tomographic image slices. Moreover, in the case of a moving organ, such as a heart, it insures that these multiple slices are all taken at the same phase in the cardiac cycle and thus that the slices are truely contiguous and give a correct three-dimensional representation of the organ.

The detector arrays used in conjunction with the above-mentioned reconfigurable x-ray sources may either be of the fixed type or of the rotating type.

Accordingly, it is an object of this invention to provide a reconfigurable tomographic x-ray scanner capable of both relatively fast single slice image scans and also relatively slower multiple slice scans.

DESCRIPTION OF THE DRAWINGS

FIG. 1 is a simplified plan view illustrating rotating detector prior art scanning configurations.

FIG. 2 is a simplified plan view illustrating prior art scanners of the fixed detector configuration.

FIG. 3 is a simplified plan view in accordance with one embodiment of the present invention in which three x-ray sources are employed in conjunction with three corresponding rotating x-ray detectors.

FIG. 6 is a simplified plan view illustrating an embodiment of the present invention in which the x-ray sources are not uniformly spaced.

DETAILED DESCRIPTION OF THE INVENTION

Figure 4:
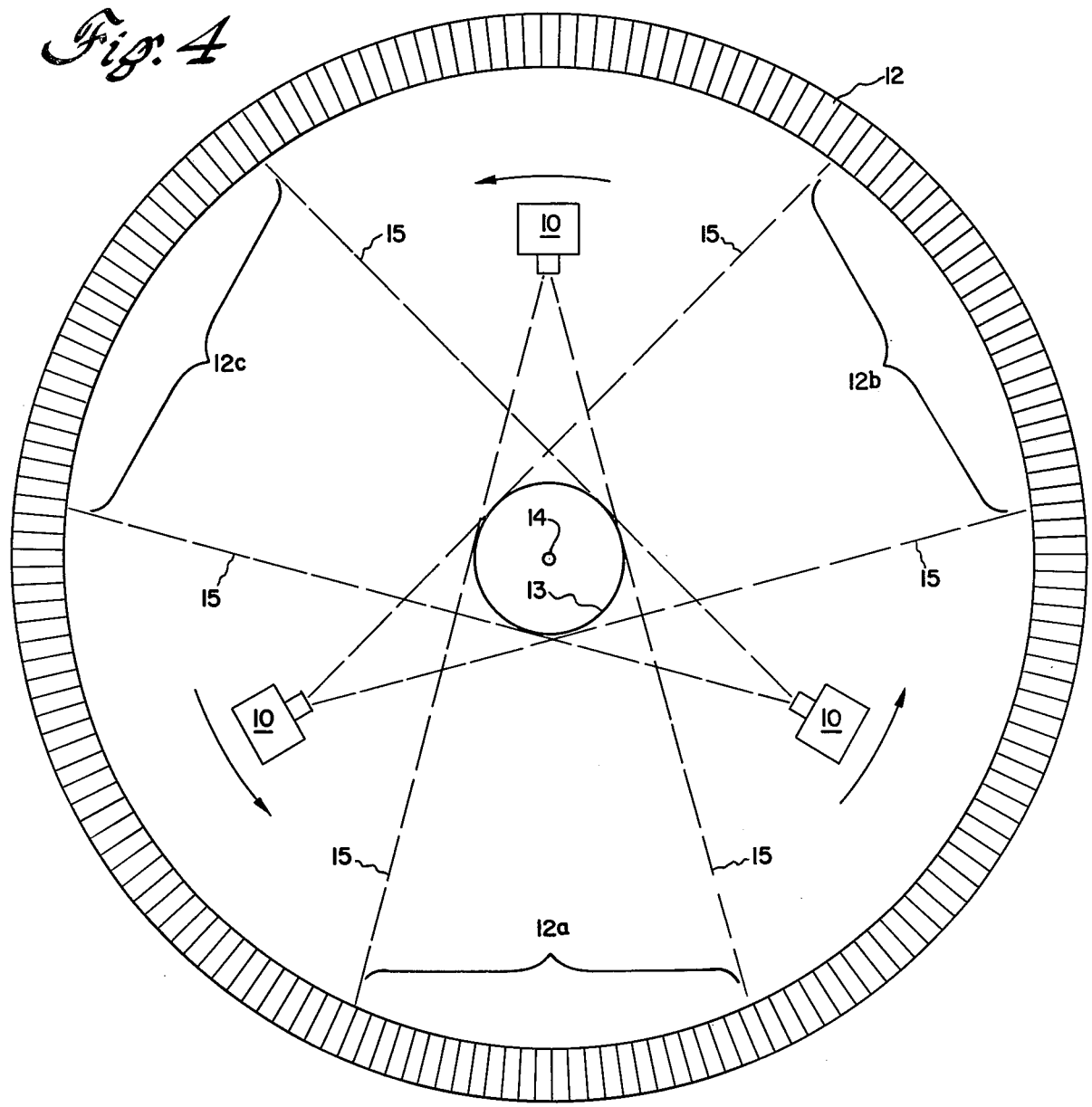
FIG. 4 is a simplified plan view illustrating another embodiment of the present invention in which three rotating x-ray sources are employed in conjunction with a fixed detector array.

FIG. 1 illustrates a typical prior art tomographic x-ray configuration. In this figure, x-ray source 10 directs a relatively flat, fan-shaped x-ray beam 15 through a patient tunnel 13 which defines a field of view. The x-rays, after modulation by the subject under study placed in the patient tunnel, then impinge upon rotating x-ray detector 11. The source 10 and detector segment 11 are adapted to move circularly about axis of rotation 14 in unison with each other. The nature of the detectors is more particularly described below.

FIG. 2 illustrates a similar prior art tomographic x-ray scan configuration in which the detectors 12 do not rotate with the x-ray source, but rather are provided in a fixed location disposed uniformly along a given circumference. As in FIG. 1, and indeed in all figures herein, the rotation is provided so that a plurality of views from different directions are seen by x-ray sources 10. The rotation may be continuous or stepped so long as the x-ray bursts are of sufficiently short duration so as to minimize blurring effects.

Because they are well known in the prior art (see, for example, U.S. Pat. No. 4,068,306) and because they are not relevant to an understanding of the present invention, the electronics associated with each individual x-ray detector are not shown in the figures. However, each individual x-ray detector herein is typically connected to a data acquisition channel which samples and holds the electrical output of the detectors at appropriate times after the firing of an x-ray burst. The resulting signal is then typically converted to digital form by an integrating single, or dual-slope analog-to-digital converter. These data, in digital form, are then stored in the memory system of a digital computer for analysis after all relevant scan directions have been sampled. The computer then analyzes these data, generating a two-dimensional array of numbers representing relative levels of x-ray absorption encountered at different locations in a plane through the body under study. This is then displayed, typically using video electronic cathode ray tube display means, and analyzed by a physician and/or a radiologist.

The rotating detector scheme of FIG. 1 has an advantage in that a smaller x-ray detector segment is required, but has the disadvantage that the x-ray detector that is provided must be rotatable in conjunction with the source 10. On the other hand, the fixed detector scheme of FIG. 2 has the advantage that the x-ray detectors are not required to rotate, but does have the disadvantage that a large number of individual detectors are provided on a circumference entirely surrounding the patient tunnel 13. In addition, in a fixed detector configuration, the x-ray source is typically confined to rotate about a circumference limited in radius by the detector array. No such limitation occurs in the rotating detector configuration of FIG. 1. However, this limitation may be mitigated by placing the x-ray source 10 in a separate plane from detector array 12. This, however, has the disadvantage of producing certain visual artifacts in the ultimate image displayed because the scan through the body under study is "wobbled". That is to say, if the x-ray source 10 is not rotating in the same plane as x-ray detectors 12, the actual scan performed through the body under study is that of a relatively flat, conically-shaped surface, rather than a flat planar surface.

FIG. 3 illustrates an embodiment of the present invention in which three rotatable x-ray sources are uniformly disposed about patient tunnel 13 and adapted to rotate about the axis of rotation 14. Each of these sources is adapted to emit a relatively flat, fan-shaped x-ray beam 15 which ultimately impinges upon rotating x-ray detector segments 11a, 11b, and 11c. While FIG. 3 illustrates the case in which three such x-ray sources and detectors are provided, any convenient number of sources and rotating x-ray detector segments may be provided. However, configurations containing three, five, or seven such source-detector pairs are presently preferred. While configurations such as those shown in FIGS. 1 and 2 are only capable of generating view data in serial fashion, the configuration of FIG. 3 generates view data in a parallel mode. For example, assuming the same rates of rotation in FIGS. 1 and 3 the scan in FIG. 3 is performed in one-third of the time. If, in FIG. 3, five source-detector pairs are provided, then the scan is accomplished in one-fifth of the time. This high-speed scanning capability is very important in the study of moving body organs such as the heart. Additionally, organs of the lower abdomen and digestive tract, which continually undergoes peristaltic motion, are readily scanned by the configuration of FIG. 3. These rapid scans are important in dynamic blood flow and cardiac output studies and also in the study of various kidney dysfunctions.

While FIG. 3 illustrates a situation in which the x-ray sources 10 are located closer to the axis of rotation 14 than are detector array segments 11a, 11b, and 11c, this need not be the case in source-detector configurations of the present invention. In particular, the x-ray sources 10 may rotate about the patient tunnel 13 at a distance from the patient tunnel 13 larger than the distance between the x-ray detector and patient tunnel 13. The configuration of choice depends upon the size of the patient tunnel 13 which defines a field of view and the detector resolution.

Of particular importance, however, is that the three source-detector pairs of FIG. 3 are not required to rotate in the same plane. This is diagrammatically illustrated in a simpilfied view in FIG. 5 in which the three sources are configured stacked one on top of the other. However, the source-detector pairs need not be aligned in the stack suggested in FIG. 5 in order to accomplish a nonplanar configuration. In particular, the source-detector pairs, as shown in FIG. 3, may each be moved independently by a different amount in a direction perpendicular to the plane of FIG. 3, preserving the same relative positions of the source-detector pairs about the patient tunnel 13. When reconfigured in this fashion, a single complete, 360 degree rotation produces the view data for three distinct contiguous, tomographic image slices. If these multiple slices are generated by the configuration of FIG. 1, then the time to perform them is tripled. Thus, the multiple slice configuration greatly increases patient throughput. The movement of the source-detector pairs into a contiguous, but nonplanar configuration, is achieved by any convenient mechanical means.

FIG. 4 illustrates an alternate embodiment of the present invention in which a fixed detector array is provided similar to that shown in FIG. 2. In this configuration, rotating x-ray sources 10 produce an x-ray fan beam 15 which impinges upon dynamically changing portions 12a, 12b, and 12c of fixed detector array 12. Likewise, the sources in FIG. 4 are reconfigurable so as not to lie in the same plane. When they are so reconfigured, rapid multiple slice images are generated. When configured in the same plane, a rapid single slice image is generated. This capability renders tomographic scanners adaptable for a variety of diagnostic modalities.

While it is recognized that multiple slices may be obtained simultaneously by a simple contiguous stacking of detector arrays on top of one another and the use of a single x-ray source, such a system produces a wobbled slice due to axial beam divergence. Again, while the wobble does produce certain artifacts, these are controllable by choosing a suitably large distance between the x-ray source and the axis of rotation. Thus, it is seen that, even though the tomographic scanner of FIG. 4, when configured in a multiple slice, nonplanar arrangement, is subject to a wobble, this wobble may be controlled by increasing the radius of rotation of the x-ray sources. The relative advantages and disadvantages of the tomographic scanner of FIGS. 3 and 4 are adequately discussed above with respect to the relative advantages and disadvantages of the scanner of FIGS. 1 and 2 with respect to the differences between fixed and rotating detector arrays.

When the tomographic scanners of the present invention are employed in a rapid, single slice planar mode, there is the possibility of introducing certain undesirable artifacts in the image displayed due to biased readings at the ends of the view. These artifacts are reduced by providing a slight over-scan and suitably averaging the duplicated information. That is to say, for example, if there are three sources provided, the instead of providing for a 120 degree scan, a 130 degree scan, for example, is provided to reduce these artifacts. Similarly, if five x-ray sources are employed, then instead of a 72 degree rotation, an 80 degree rotation may be provided.

As mentioned above, the detectors basically function to convert analog x-ray intensity information into electrical signals. The x-ray detectors, themselves, are typically one of three designs. For example, the detector array may comprise an ionization detector formed by disposing a high pressure noble gas, such as xenon, between electrically charged metal plates. Alternately, the detector may be comprised of a scintillator material used in conjunction with a photodiode. Additionally, a scintillator material may be used in conjunction with a photomultiplier. Any of these detector designs may be used in conjunction with the above-described embodiments of the present invention.

Figure 5:
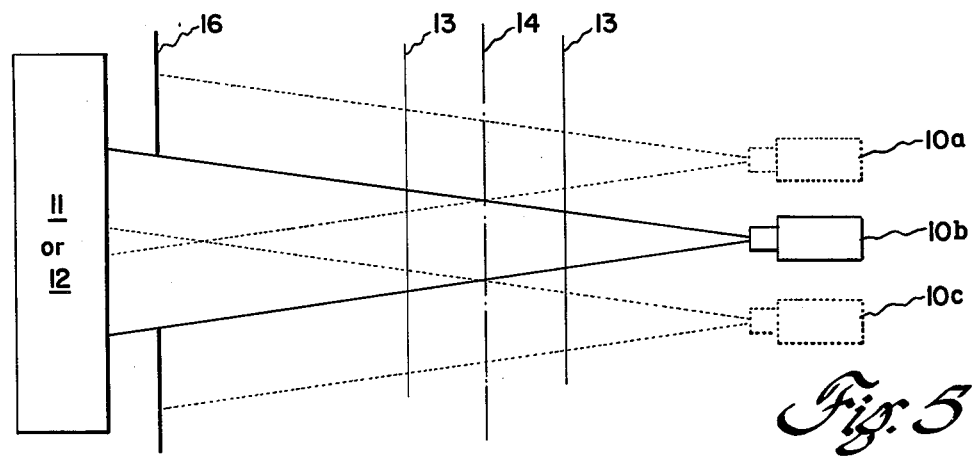
FIG. 5 is a simplified side elevation view illustrating the configuration of the present invention when multiple slice images are being generated.

In FIG. 5, a three source embodiment of the present invention is shown. However, for simplicity, the sources are shown at the same angular location; sources 10a and 10c are shown in dotted form though to emphasize that they are actually disposed at different angular positions about the axis of rotation 14. An optional radio opaque baffle 16 is disposed between x-ray sources 10 and either fixed x-ray detectors 12 (as in FIG. 4) or rotating x-ray detectors 11 (as in FIG. 3). The baffle rotates in front of the detector to block scatter from adjacent slices and is designed to pass the desired x-ray fan beam.

At any instant, the detector is in the fan of only one of the x-ray sources. The wobble that occurs in the multiple contiguous slice configuration of FIGS. 5 and 4, while tolerable, is correctable by providing an x-ray detector which is active along a sufficiently long axial dimension such that when the x-ray fan beam sources are operated in this multiplanar mode, all of the x-ray fan beams impinge upon an active portion of the detector. Prior art x-ray tomographic scanners do not possess this capability.

FIG. 6 illustrates yet another operating modality of the present invention. In FIG. 6, sources 10 are not disposed uniformly about the periphery of the patient tunnel 13 or the periphery of the fixed detector array 12. For example, in a configuration with the sources spaced 60 degrees apart, a complete tomographic image may be reconstructed using data collected in a scan rotation of only 180 degrees plus the x-ray fan beam angle $\theta$. This configuration permits a near doubling in speed. It also permits a reduction in the number of detector cells by omitting need for those cells not receiving radiation in a given scan and by alternately reversing the scan direction between clockwise and counterclockwise. Of course, the entire circular array of detector cells 12 may be used by initiating subsequent scans at those angular positions assumed at the end of previous scans, without any reversal in scan rotation direction. The sources are independently positionable about the circumference so that a configuration as shown in FIG. 6 may be easily reconfigured into the system illustrated in FIG. 3.

Additionally, FIG. 6 illustrates analog-to-digital converter 20 which receives signals from the detector cells. These signals are converted to digital form and transmitted to digital computer 21 which operates on the digital signals, in well-known fashion, to produce signals suitable to drive display means 22, converter 20, computer 21, and display 22 and are shown only in FIG. 6 for convenience but are similarly provided in the embodiments shown in the other figures.

From the above, it can be appreciated that the invention herein provides for a flexible, adaptable and reconfigurable computerized tomographic x-ray scanner capable of operating in several diagnostic modalities. In a first configuration, the imaging system disclosed herein is capable of producing rapid single slice images useful in studies of moving bodily organs, such as the heart. In a second, nonplanar configuration, the imaging system herein is capable of generating rapid multiple slice images, with minimal impact upon patient throughput.

While this invention has been described with reference to particular embodiments and examples, other modifications and variations will occur to those skilled in the art in view of the above teachings. Accordingly, it should be understood that, within the scope of the appended claims, the invention may be practiced otherwise than is specifically described.

The invention claimed is:

1. In a computerized tomographic imaging system including:
   x-ray source means;
   x-ray detection means functioning to convert x-ray radiation from said x-ray source means to analog electrical signals, said radiation passing through and being variably absorbed by a body under study, said body being disposed between said x-ray source and said detection means;
   means to convert said analog electrical signals to digital signals; and
   computer means to operate on said digital signals so as to generate signals representing relative degrees of x-ray radiation absorption by said body under study; the improvement wherein:
   the x-ray source means comprises a plurality N of x-ray sources rotatable about an axis of rotation and disposed along a circumference surrounding said body to be studied, with at least (N-1) of said sources being independently movable in a direction parallel to said axis of rotation, whereby the imaging system is reconfigurable from a rapid single slice mode to a multiple slice mode.

2. The computerized tomographic imaging system of claim 1 in which the detection means comprises a nonrotating array of x-ray detectors arranged on a circumference greater than the circumference along which the x-ray radiation sources are disposed, and adapted to be illuminated by x-ray radiation from said x-ray sources from positions occupied by said x-ray sources.

3. The computerized tomographic imaging system of claim 1 in which the detection means comprises a plurality of detection segments rotatable about the axis of rotation and disposed along a circumference surrounding said body to be studied, each said segment receiving x-ray radiation from a unique x-ray source disposed radially opposite said detection segment.

4. The computerized tomographic imaging system of claim 3 in which the detector segments are independently movable in a direction parallel to said axis of rotation in unison with the movement of said x-ray sources.

5. The computerized tomographic imaging system of claim 1 further comprising radio opaque baffle means disposed between said detection means and said body under study, said baffle means being adapted to limit the radiation admitted to said detection means to that radiation emanating from a single x-ray source, whereby radiation scatter from adjacent sources is blocked.

* * * * *